(12) United States Patent
Platt et al.

(10) Patent No.: US 10,650,808 B1
(45) Date of Patent: May 12, 2020

(54) DYNAMICALLY CONFIGURABLE INTERFACE FOR STRUCTURED NOTE DICTATION FOR MULTIPLE EHR SYSTEMS

(71) Applicant: NoteSwift, Inc., Boston, MA (US)

(72) Inventors: Timothy Platt, Andover, MA (US); Allan Stratton, Wakefield, MA (US)

(73) Assignee: Noteswift, Inc., Boston, MA (US)

( * ) Notice: Subject to any disclaimer, the term of this patent is extended or adjusted under 35 U.S.C. 154(b) by 64 days.

(21) Appl. No.: 15/895,361

(22) Filed: Feb. 13, 2018

Related U.S. Application Data

(60) Provisional application No. 62/458,768, filed on Feb. 14, 2017.

(51) Int. Cl.
| | |
|---|---|
| *G01L 15/00* | (2006.01) |
| *G10L 15/18* | (2013.01) |
| *G16H 10/60* | (2018.01) |
| *G10L 15/04* | (2013.01) |
| *G06F 3/0482* | (2013.01) |
| *G10L 15/22* | (2006.01) |
| *G06F 16/2458* | (2019.01) |
| *G06F 40/284* | (2020.01) |

(52) U.S. Cl.
CPC ........ *G10L 15/1815* (2013.01); *G06F 3/0482* (2013.01); *G06F 16/2468* (2019.01); *G06F 40/284* (2020.01); *G10L 15/04* (2013.01); *G10L 15/1822* (2013.01); *G10L 15/22* (2013.01); *G16H 10/60* (2018.01)

(58) Field of Classification Search
CPC .......... G10L 15/18; G10L 15/22; G16H 10/60
USPC ........................................................ 704/270
See application file for complete search history.

(56) References Cited

U.S. PATENT DOCUMENTS

| | | | |
|---|---|---|---|
| 6,374,226 B1 | 4/2002 | Hunt et al. | |
| 6,999,931 B2 | 2/2006 | Zhou | |
| 7,996,223 B2 | 8/2011 | Frankel et al. | |
| 8,560,300 B2 | 10/2013 | Ferruci et al. | |
| 8,670,987 B2 | 3/2014 | Bergl et al. | |
| 8,694,335 B2* | 4/2014 | Yegnanarayanan | G16H 10/60 705/2 |
| 2003/0105638 A1* | 6/2003 | Taira | G06F 17/2881 704/275 |
| 2007/0208567 A1* | 9/2007 | Amento | G10L 15/22 704/270 |
| 2011/0060584 A1* | 3/2011 | Ferrucci | G06F 17/273 704/9 |
| 2013/0035961 A1* | 2/2013 | Yegnanarayanan | G16H 10/60 705/3 |
| 2018/0308583 A1* | 10/2018 | Yegnanarayanan | G16H 50/20 |

* cited by examiner

*Primary Examiner* — Daniel Abebe
(74) *Attorney, Agent, or Firm* — Patterson Thuente Pedersen, P.A.

(57) ABSTRACT

Systems and methods for providing a dynamically configurable interface for structured note dictation input for one or more electronic health record (EHR) systems generally comprise a dictation user interface, a dictation management subsystem, and at least one EHR system having a plurality of electronic medical records. The dictation management subsystem generally comprises a computing device configured to moderate the recognized text for a particular EHR system and particular electronic health record.

20 Claims, 15 Drawing Sheets

DYNAMICALLY CONFIGURABLE INTERFACE FOR STRUCTURED NOTE DICTATION FOR MULTIPLE EHR SYSTEMS

RELATED APPLICATION

This application claims the benefit of U.S. Provisional Application No. 62/458,768 filed Feb. 14, 2017, which is hereby fully incorporated herein by reference.

TECHNICAL FIELD

Embodiments relate generally to computer systems for dictation related to Electronic Health Records (EHRs). More particularly, embodiments relate to systems and methods for SOAP (Subjective, Objective, Assessment, and Plan) note dictation and entry into EHR systems.

BACKGROUND

As early as the 1930's, researchers have been investigating the science of speech perception. As this area of linguistics has matured, a number of dictation tools and dictation post-processing tools have been developed. In general, existing speech recognition tools are directed towards free text dictation and provide very minimal navigation capabilities, which results in added time and frustration for users.

At the same time, EHRs, which provide an electronic version of a patient's medical history, have developed to provide a more seamless flow of information within a digital health care infrastructure. Integrating dictation into EHRs has been necessitated due to budget pressures, quality care considerations, and compliance risks, among other concerns. However, existing dictation systems are often difficult to use in an EHR context due to the structure often required for particular EHR sections, and moreover, between unique EHR systems.

For example, U.S. Pat. No. 6,374,226, entitled "System and method for interfacing speech recognition grammars to individual components of a computer program" describes a number of speech controller modules corresponding to program components within a computer program. Each speech controller module supports a speech recognition grammar having at least one rule, where the speech recognition grammar provides an interface to operations on the corresponding program component. A rule may include a reference to another local rule, or to a rule in a different speech recognition grammar, in which case a "link" to the other rule is formed. In this way, the disclosed system allows rules from the same or different grammars to be combined together, in order to build complex grammars. However, such a solution is impractical for an EHR context because separate rules must be pre-established and linked for every unique EHR-entry section.

U.S. Pat. No. 6,999,931, entitled "Spoken dialog system using a best-fit language model and best-fit grammar" describes using likelihood scores from a large vocabulary continuous speech recognizer (LVCSR) to select the best-fit language model (LM) among a general-task LM and dialog-state dependent LMs. However, such a solution requires LMs to be predetermined for each dialog state.

U.S. Pat. No. 7,996,223, entitled, "System and method for post processing speech recognition output" describes a post processing system configured to implement rewrite rules and process raw speech recognition output or other raw data according to those rewrite rules. The application of the rewrite rules may format and/or normalize the raw speech recognition output into formatted or finalized documents and reports. However, such systems lack any user interfacing functionality that might allow the user to adjust to the system and the system to adjust to the user.

U.S. Pat. No. 8,670,987, entitled "Automatic speech recognition with dynamic grammar rules" describes an automatic speech recognition ('ASR') engine having a speech recognition grammar that defines at run time a dynamic rule of the grammar that is not to be processed by the ASR until after the at least one static rule has been matched. However, the dynamic rules system describes a set of interrelated grammar rules that rely on other rules already matched and use a sequential order-based dependency for processing the input stream.

Therefore, there is a need for systems and methods that can more efficiently integrate dictation systems into EHR record-keeping systems and solve the dictation problems exemplified by the patents described above.

SUMMARY

In various embodiments, a dynamically configurable interface for structured note dictation input for one or more EHR systems generally comprises a dictation user interface, a dictation management subsystem, and at least one EHR system having a plurality of electronic medical records. The dictation management subsystem generally comprises a computing device configured to moderate the recognized text for a particular EHR system (and accordingly, a particular electronic health record).

In certain embodiments, dictation management subsystems can be implemented in a one-to-many relationship with EHR systems. For example, a single embodiment of a dictation management subsystem described herein can interface with multiple types and variations of EHR systems. Dictation management subsystems therefore allow for EHR-agnostic note dictation.

In other embodiments, users need not set up rules or grammars for EHR entry. Rather, embodiments of the system use algorithms for scoring and fuzzy matching to dynamically and automatically augment the dictated text into user-selectable responses and subsequent entry into proper EHR fields. In some embodiments, intelligent segmentation allows continuous speech with only modestly constrained grammar.

A SOAP note is a method of documentation employed by health care providers to write out notes using a predefined structure which typically includes subjective, objective, assessment, and plan information. SOAP notes have sections that correspond to sections in some EHRs (e.g. current diagnosis, past medications, etc.). Intelligent segmentation using knowledge of SOAP notes structures additionally provides neighborhood context for segmented phrases and drives queries more intelligently by using the characteristics of the section of the SOAP note that is being dictated.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIG. 5A is a screenshot of a patient summary window and a SOAP note dictation entry window, according to an embodiment.

FIG. 5B is a screenshot of a patient summary window and a SOAP note dictation entry window with text entered using a dictation interface, according to an embodiment.

FIG. 5C is a screenshot of a patient summary window and a SOAP note dictation entry window in the background and a correction window for a first possibly ambiguous, generic, or incorrectly recognized term in the foreground, according to an embodiment.

FIG. 5D is a screenshot of a patient summary window and a SOAP note dictation entry window in the background and a correction window for a second possibly ambiguous, generic, or incorrectly recognized term in the foreground, according to an embodiment.

FIG. 5E is a screenshot of a medication details window, according to an embodiment.

FIG. 5F is a screenshot of a corrected patient summary window and a SOAP note dictation entry window for entry into an EHR, according to an embodiment.

Figure 1:
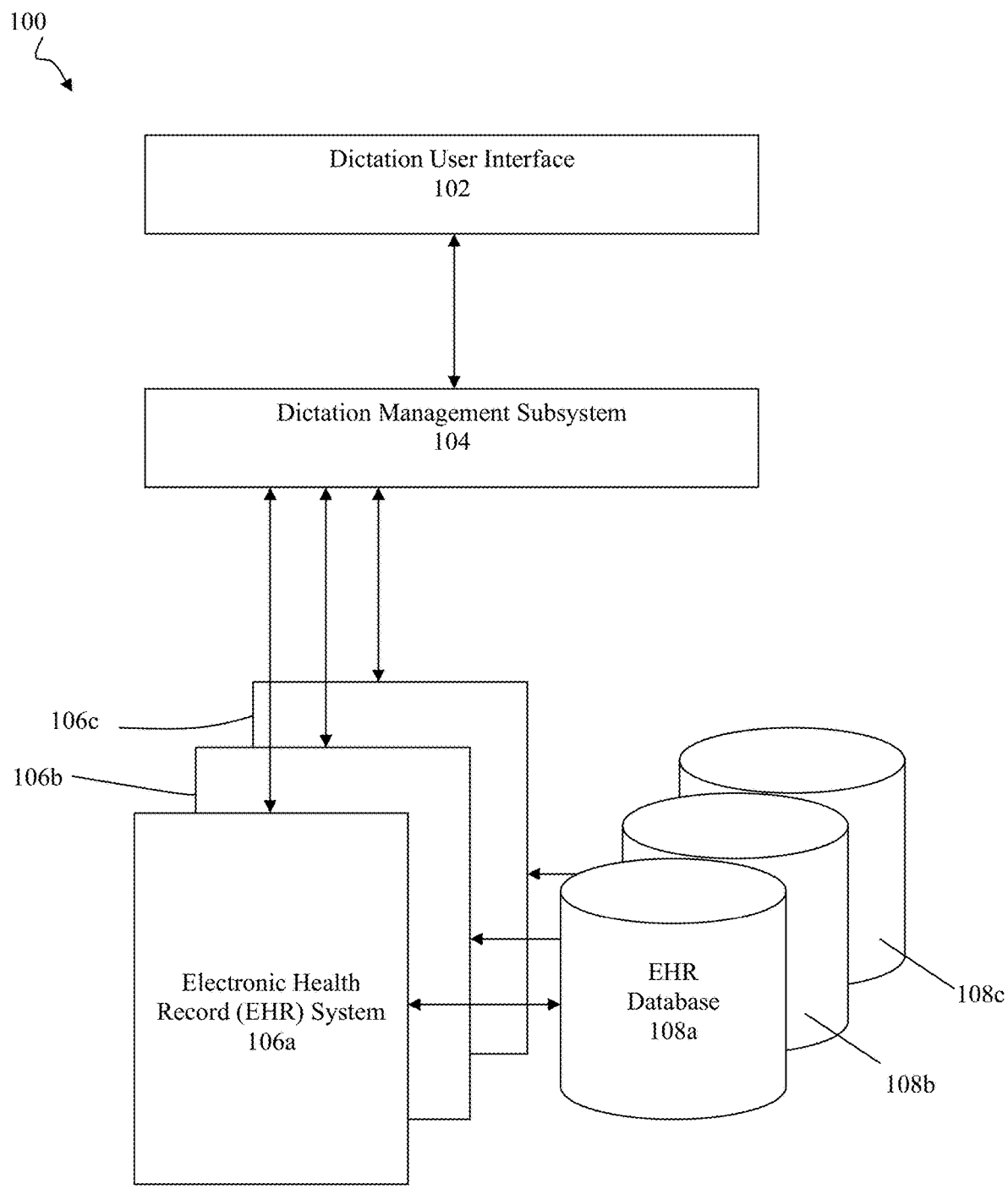
FIG. 1 is a block diagram of a system for dynamically configurable note dictation interface with one or more EHRs utilizing a dictation management subsystem, according to an embodiment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Various terminology is used herein to describe embodiments.

The term "discrete data" refers to a very particular selection in an EHR, or in an exchangeable record produced by that EHR. An example of discrete data is a standard diagnostic code (ref ICD10). In embodiments, another example of discrete data is a choice of an item from a list presented in the EHR. Using discrete data in medical records allows systems to represent such data in machine readable forms, such as in memory or in exchange (exported) format as a file or data stream.

The term "structured data" can represent a collection of discrete data for a clinical document. An example of a clinical document is a doctor's encounter note with a patient. In a structured document, discrete data items are represented either explicitly or as a set of name-value pairs. As an example one might have "Primary diagnosis: Essential Hypertension." Additionally, name-value pairs can be grouped in a hierarchy for easy access or automatic processing. For example, "Ibuprofen" may be contained in a "previous medication" section whereas "Albuterol" may be contained in a list of prescriptions "to be filled by the patient."

The term "clinical item" can include an entry in a clinical document. A clinical item can be discrete (structured) or free text, depending on the context. A particular clinical item can even have both discrete data and free text associated with it. An example clinical item can be an ICD10 code for the primary diagnosis with an associated "Physician's note" or "Impression."

The term clinical document can include a collection of clinical items that collectively represent a report, assessment, result, etc. of a clinical visit, test battery, or status report. An example of a clinical document is a Doctor's note of an encounter with a patient.

Referring to FIG. 1, a block diagram of a system for dynamically configurable note dictation interface with one or more EHRs utilizing a dictation management subsystem is depicted, according to an embodiment. System 100 generally comprises a dictation user interface 102, a dictation management subsystem 104, and at least one EHR system 106. As will be described, dictation management subsystem 104 can operate in a one-to-many relationship with unique EHR systems, such as EHR systems 106a-106c.

Embodiments of the system 100, and the corresponding methods of configuring and operating the system 100, can be performed in cloud computing, client-server, or other networked environment, or any combination thereof. The components of the system can be located in a singular "cloud" or network, or spread among many clouds or networks. End-user knowledge of the physical location and configuration of components of the system is not required.

As will be described, the system and/or its components or subsystems can include computing devices, microprocessors, modules and other computer or computing devices, which can be any programmable device that accepts digital data as input, is configured to process the input according to instructions or algorithms, and provides results as outputs. In an embodiment, computing and other such devices discussed herein can be, comprise, contain or be coupled to a central processing unit (CPU) configured to carry out the instructions of a computer program. Computing and other such devices discussed herein are therefore configured to perform basic arithmetical, logical, and input/output operations.

Computing and other devices discussed herein can include memory. Memory can comprise volatile or non-volatile memory as required by the coupled computing device or processor to not only provide space to execute the instructions or algorithms, but to provide the space to store the instructions themselves. In embodiments, volatile memory can include random access memory (RAM), dynamic random access memory (DRAM), or static random access memory (SRAM), for example. In embodiments, non-volatile memory can include read-only memory, flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of the invention.

In embodiments, the system or components thereof can comprise or include various modules or engines, each of which is constructed, programmed, configured, or otherwise adapted, to autonomously carry out a function or set of functions. The term "engine" as used herein is defined as a real-world device, component, or arrangement of components implemented using hardware, such as by an application specific integrated circuit (ASIC) or field-programmable gate array (FPGA), for example, or as a combination of hardware and software, such as by a microprocessor system and a set of program instructions that adapt the engine to implement the particular functionality, which (while being executed) transform the microprocessor system into a special-purpose device. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each engine can be realized in a variety of physically realizable configurations, and should generally not be limited to any particular implementation exemplified herein, unless such limitations are expressly called out. In addition, an engine can itself be composed of more than one sub-engines, each of which can be regarded as an engine in its own right. Moreover, in the embodiments described herein, each of the various engines corresponds to a defined autonomous functionality; however, it should be understood that in other contemplated embodiments, each functionality can be distributed to more than one engine. Likewise, in other contemplated embodiments, multiple defined functionalities may be implemented by a single engine that performs those multiple functions, possibly alongside other functions, or distributed differently among a set of engines than specifically illustrated in the examples herein.

Dictation user interface 102 generally comprises a user interface in which a user can dictate commands, text, or other verbal inputs into system 100. Dictation user interface 102 can comprise a microphone and speech-to-text recognition software. In an embodiment, dictation user interface 102 further provides an abstraction layer for programmatic access to the speech-to-text recognition software. For example, an abstraction layer can be provided for DRAGON MEDICAL recognition software access. In embodiments, additional abstraction layers can be provided for other speech-to-text recognition software access. Dictation user interface 102 therefore provides a plug-in architecture that allows switching between different speech recognition providers by providing an abstraction layer on top of the particular provider.

Dictation management subsystem 104 generally comprises a computing device configured to moderate the recognized text for a particular EHR system 106 and particular electronic health record. Dictation management subsystem 104 is operably coupled to dictation user interface 102 and at least one EHR system, such as EHR system 106a. Dictation management subsystem 104 is described further below with respect to FIGS. 2-3.

EHR system 106a generally comprises a computing system for electronic health record management and storage. As shown, each EHR system can comprise one or more database of EHR records. For example, EHR system 106a comprises EHR database 108a. EHR database 108a can comprise storage for a plurality of EHRs. Likewise, EHR system 106b comprises EHR database 108b and EHR system 106c comprises EHR database 108c. In embodiments, each EHR system 106a-106c can include an EHR that is structured or organized differently than each of the other EHRs.

Figure 2:
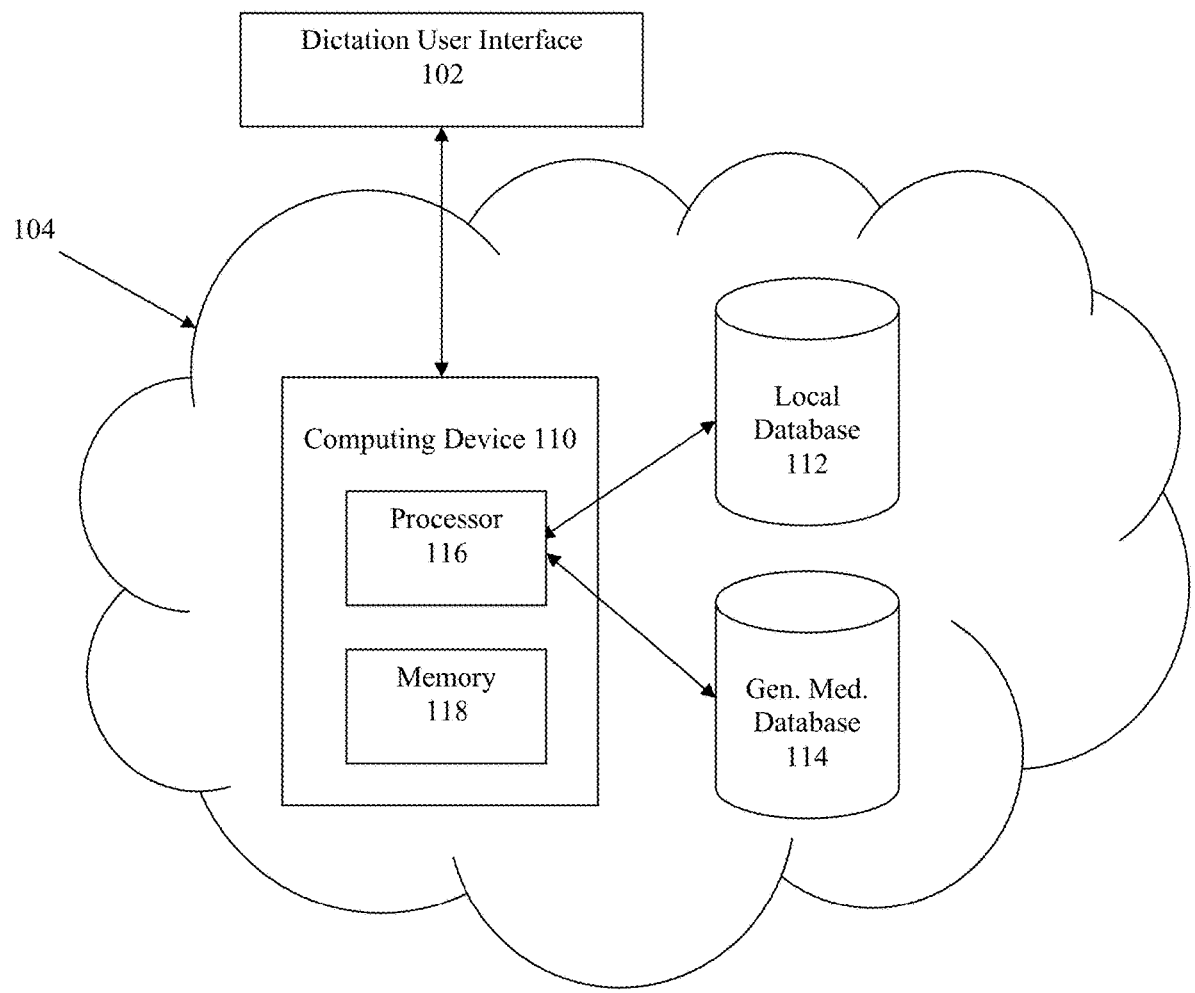
FIG. 2 is a block diagram of a dictation management subsystem, according to an embodiment.

Referring to FIG. 2, a block diagram of a dictation management subsystem is depicted, according to an embodiment. For example, dictation management subsystem 104 is depicted. Dictation management subsystem 104 generally comprises a computing device 110, a local database 112, and a general medical database 114.

Computing device 110 can comprise a computer other similarly capable computing or digital device. One skilled in the art will readily appreciate that computing device 110 can be implemented in a singular "cloud" or network, or spread among many clouds or networks. Likewise, computing device 110 can further be a component of EHR system 106a, or implemented as a web server accessed using a browser with a remote device, such as a smart phone, tablet, or laptop. For ease of explanation, computing device 110 is described with as a single computing device.

Computing device 110 generally comprises a processor 116 and memory 118 operably coupled to processor 116. Processor 116 is configured to carry out the instructions of the various engines for dictation management stored on memory 118. In embodiments, memory 118 can further comprise cache for recent or short term storage of queries and functions of the various engines. Processor 116 can be operably coupled to local database 112 and general medical database 114.

Local database 112 is configured to store commonly used data, such as common vocabulary or diagnosis codes for common diagnoses. In particular, local database 112 comprises a database configured to the generally-tailored data associated with open-ended questions and answers. Local database 112 can be a general purpose database management storage system (DBMS) or relational DBMS as implemented by, for example, Oracle, IBM DB2, Microsoft SQL Server, PostgreSQL, MySQL, SQLite, Linux, or Unix solutions, in embodiments.

General medical database 114 is configured to store medical data, including terms and medical use. Likewise, general medical database 114 can be a general purpose database management storage system (DBMS) or relational DBMS as implemented by, for example, Oracle, IBM DB2, Microsoft SQL Server, PostgreSQL, MySQL, SQLite, Linux, or Unix solutions, in embodiments.

Figure 3:
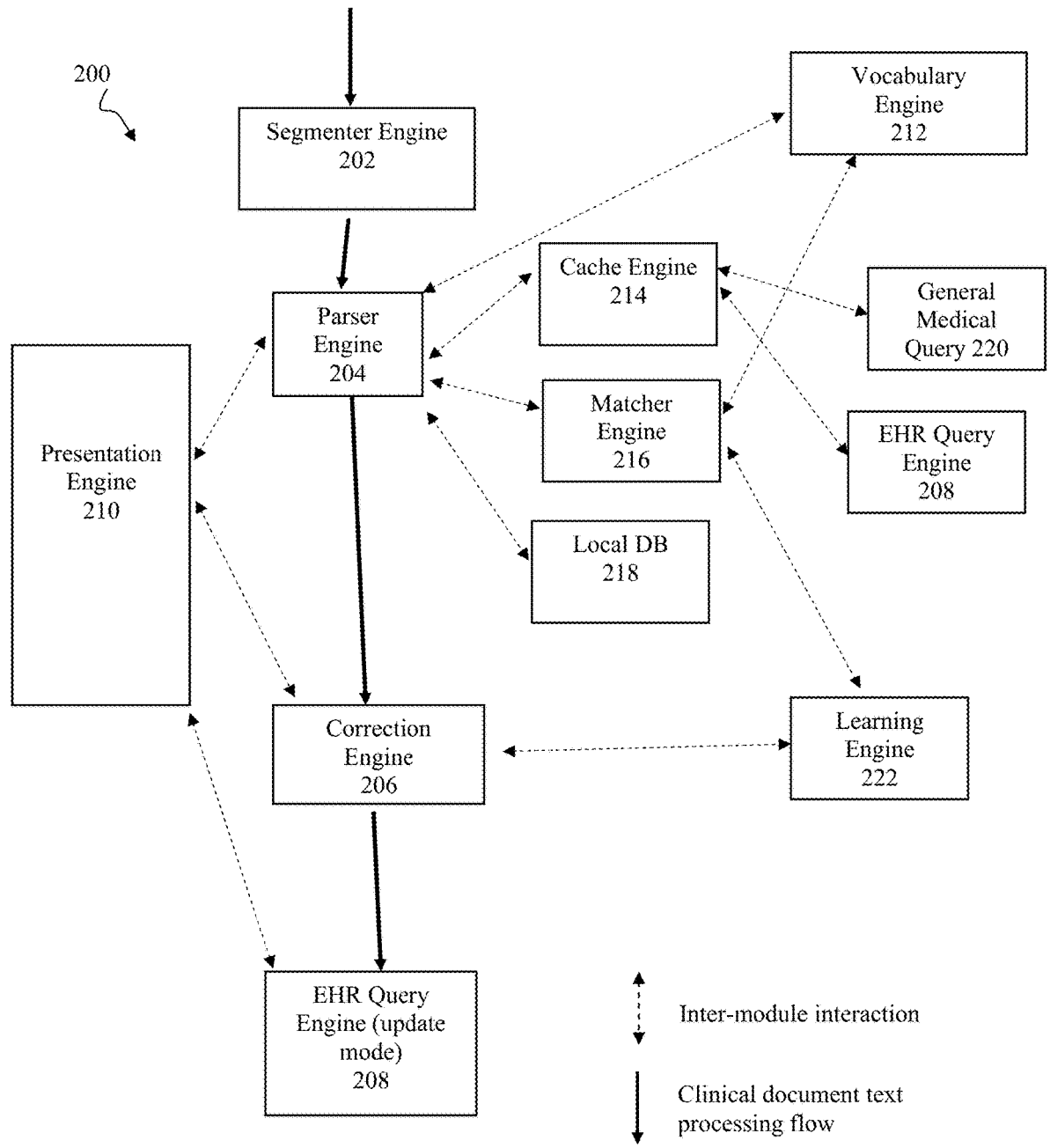
FIG. 3 is a block diagram of a dictation management subsystem, according to an embodiment.

Referring to FIG. 3, a block diagram of a dictation management subsystem 200 is depicted, according to an embodiment. Dictation management subsystem 200 can be implemented by processor 116 and memory 118 described above with respect to computing device 110. For example, dictation management subsystem 200 can be substantially similar to dictation management subsystem 104.

FIG. 3 depicts both inter-engine interactions, as denoted by dotted lines, as well as clinical document text processing flow, as denoted by solid lines. Referring to the clinical document text processing flow, dictation management subsystem 200 generally comprises a segmenter engine 202, a parser engine 204, a correction engine 206, and an EHR query engine 208. Dictation management subsystem 200 can further comprise a number of other engines and hardware structures, such a presentation engine 210, vocabulary database 212, cache engine 214, matcher engine 216, local database 218, general medical query engine 220, and learning engine 224.

Segmenter engine 202 is configured to receive as input the spoken clinical text. For example, segmenter engine 202 can receive data directly from dictation user interface 102, or an abstraction layer implemented by dictation user interface 102. In another embodiment, dictation management subsystem 104 and particularly, segmenter engine 202 is configured to receive spoken text imported from a text file.

Segmenter engine 202 is configured to segment the clinical text into lines and tokens. In an embodiment, lines and tokens correspond to word delineations. In an embodiment, segmenter engine 202 parses lines and words but does not parse punctuation, as punctuation can be processed easier in later steps.

Segmenter engine 202 can further identify section headers. Section headers can be marked to allow the text in a given section to be quickly accessed by other engines of dictation management subsystem 200 and allow for the identification of the EHR section in which a particular token is located. For example, section headers can begin with a keyword or keywords and a colon such as "Plan:" or "Diagnosis:". Segmenter engine 202 can therefore identify headers before parser engine 204 operates in order to mark identifier of sections for particular text segments.

Parser engine 204 is configured to receive the output of segmenter engine 202 and conduct additional processing. In an embodiment, parser engine 204 can access a small list of common words and a list of common medical words in a vocabulary engine 212.

Vocabulary engine 212 comprises language-specific data. Vocabulary engine 212 can be used to determine if a word represents a frequent English word such as "and", "or", "with", etc. or if word is a common Medical term such as "systemic." In some embodiments, vocabulary engine 212 comprises a discrete engine from local database 218. In other embodiments, vocabulary engine 212 comprises the same engine or data storage as local database 218.

Using vocabulary engine 212, as well as line breaks and punctuation, parser engine 204 can identify target phrases, or word sequences within the clinical document text as potential meaningful medical phrases.

In an embodiment, parser engine 204 can access local database 218. Local database 218 can comprise information available to parser engine 204 for efficient query of very common items. For example, diagnoses codes for some of the most common diagnoses can be stored in local database 218.

In an embodiment, parser engine 204 can use general medical query engine 220 to see if a phrase is a match for a medical concept in a local database or in a public database. General medical query engine 220 is configured to query local and/or public medical term databases to see if a given phrase is found in common medical use. In certain embodiments, databases are capable of retuning multiple medical terms for a given input based on whether the match must be exact or not. In addition, general medical query engine 220 can use context from within the clinical document to limit the portions of the databases searched so as to limit the return results and better target the expected source section of the clinical document for a given phrase. A particular medical database might optionally, or in addition, return a code for a return value of a query, such as ref ICD10, LINC, or CPT. In turn, general medical query engine 220 can retrieve information from EHR query engine 208 as to whether and where EHR query engine 208 can accept a given standard code to query for a given clinical item. As a result, general medical query engine 220 can be automatically configured for the currently-active EHR. Note in FIG. 3, EHR query engine 208 is shown twice for ease of illustration. In the link between cache engine 214, EHR query engine 208 is used for queries and data retrieval, whereas in the link to correction engine 206, EHR query engine 208 is used for updating.

Embodiments of EHR query engine 208 are tailored specific to the EHR of the particular EHR system for which EHR updates are desired. As such, the user need not worry about which EHR system or EHR the dictation management subsystem 200 is interfaced. In an embodiment, EHR query engine 208 comprises a programmatic interface to the particular EHR. As described above, parser engine 204 can use EHR query engine 208 to find objects in the EHR that match a phrase marked as an object in the clinical document by parser engine 204 using general medical query engine 220. This query to EHR query engine 208 can often be clinical document section-specific. In addition, EHR query engine 208 can provide information specific to a particular patient such as age, gender, and existing conditions. Patient-specific information can be used to flag a provisional identification of a clinical item in the original text as redundant or inconsistent. For example, in an embodiment, an object marked as a "diagnosis" in the clinical document will be queried only in the diagnosis lists of the EHR. Matcher engine 216 can be utilized to order the returned lists from the EHR. In embodiments, as will be described, matcher engine 216 can be configured for matching EHR items with additional rules that are specific to the given EHR and section. The returned list for each object in the clinical document is scored, ranked, and queued up for setting into the EHR as a final result.

In an example of the particular tailoring to EHR systems, embodiments of matcher engine 216 can be programmed with particular understanding of those systems. For example, matcher engine 216 can understand that "XRAY" is typically used in the databases accessed by general medical query engine 220 but that the given EHR typically uses "X-RAY" or even "XR". In this case, matcher engine 216 can be dynamically loaded with special equivalency match rules. This rule or rules then are only used in that context of querying that EHR. The EHR can return all lists of procedures with an appended CPT code, e.g. xyz (63901) and EHR query engine can then use matcher rules to score this particular insertion rule at low or zero match.

In embodiments, the program interface to the EHR via EHR query engine 208 can include add, update, and query methods. As such, as described above, EHR query engine 208 both query and update the EHR. EHR query engine 208 is therefore configured as an abstraction layer over the program interface of the actual EHR. In this manner, a different EHR query engine 208 can be implemented using the same abstraction layer. Therefore, no change in the other engines of dictation management subsystem 200 are required when targeting a different EHR. Users of dictation management subsystem 200 are therefore presented a single mode of use, which simplifies user documentation and user training, in contrast to traditional EHR interfaces that require a significantly different set of mouse pointing, clicking and/or typing to enter the same discrete data item.

Matcher engine 216 is configured to score any matches that come back from the respective databases. If the best match is within a given threshold, the phrase is marked as an object to be sent to EHR query engine 208. If there is no match or if the match is outside the given threshold, the words included in the phrase can be adjusted by adding or subtracting words at the end and/or the beginning of the phrase. In embodiments, general medical query engine 220 can then be re-queried to see if the adjusted phrase matches. Adjustment in this way can be limited by any surrounding phrases marked by previous matches or by lexical constraints such as line breaks and punctuation for rules that are context sensitive to the relevant section of the clinical document. Adjustment by addition can be recursive for any number of available words. Likewise, adjustment by subtraction can be recursive to subtract a first word, then a second word, and so on.

Matcher engine 216 is configured to compare a first sequence of one or more words against a second sequence of one or more words. Matcher engine 216 returns a score for the match which indicates the closeness of the match. Matcher engine 216 can therefore match a given phrase against a list of phrases and rank the list of phrases in terms of how close they match the given phrase. Matcher engine 216 can further determine how close a given match is to the first match (for example, the second best match compared to the first match). Matcher engine 216 can further compare phrases that are not exact matches and can take into account insertions, deletions, and word reordering. Matcher engine 216 can be configured to score insertions and deletions differently based on whether the inserted or deleted word is a common English word such as "with" compared to a medical term that may be a more significant insertion or deletion.

Matcher engine 216 can include base level rules for comparing but can be dynamically augmented with context-specific rules for scoring matches. For example, a list of abbreviations can be loaded into the matcher engine 216. In such an embodiment, "CBC" can match "Complete Blood Count" with a zero cost to the overall match score of the longer phrases for containing the abbreviation and expansion. Similar dynamic rules are being able to match "Lipase (80053)" against "Lipase" by indicating an insertion of "(xxx)" at an end for a zero cost to the scoring sub-match. In other examples, "2" matches "II" and "hypertension" matches "essential hypertension," but only in the contexts where it is expected. Using this technique, matcher engine 216 can match a given candidate phrase to a list of potential target phrases with a smaller set of simpler rules than then what would be needed by the necessary set of grammar or transformation rules.

In particular, matcher engine 216 is configured to assign a score that represents the similarity or closeness of one m-element sequence of items to another n-element sequence of items. In the general case, m does not equal n. The score or closeness represents whether the sequences share the same elements, but also a measure of how the order of the elements match. The closeness is represented as a numerical score so that any two such scores can be compared to determine which relationship is closer. In this way, for example, sequence A can be matched to sequence B and also A to sequence C. The scores of the two matches can be compared to determine if A is a closer match to B or C. In general, the compared sequences can be sequences of any set of items that can also be compared one for one within the set. As an example, for purposes of explanation, the sequences considered here are sequences of words. Also, for purposes of explanation, lower scores are assigned to higher level of closeness. Additionally, for explanation, decimal values can be representative of scores such that 0.0 represents a perfect match.

Matcher engine 216 accomplishes this by assigning a score to a given match by summing the scores of a number of local matches. In a very simple example, the sequence "a very good day" can be matched to "a good day". Multiple ways of segmenting the sequences into local scoring areas exist. Once segmented into local scoring areas, the scores can be tabulated and summed. For example, entire sequences can be matched together which, in our example is a 4-to-3 local match. Another is to match "a" to "a", "very" to {empty}, "good" to "good" and "day" to "day". As a result, there are 4 local scores to be tabulated and summed. The "very" to {empty} represents an insertion (or deletion) error depending on the sequence one considers as the reference. If the insertion error was given a value 1.0 and the others were assigned a value of 0.0, then the summed score of the entire match would be 1.0. One could also consider matching "a" to "a", "very good" to "good" and "day" to "day". This is then 3 local matches comprising the entire match. In this example, the exact match rule can be applied, but plainly, a rule to score a 2-to-1 match is required. Consider then the sequences "a very good day" and a "a very bad day". A simple local match segmentation would be to match "a" to "a", "very" to "very", "good" to "bad" and "day" to "day". This is a set of 4 local scores. Three are exact matches and can be scored as before, the remaining is a replacement error, and for simplicity can be assigned a score of 1.0 and thus the score for the entire match would be 1.0 again. A replacement error can be assigned a fixed score but it can also be based on the similarity of the items. So in comparing "a very good day" to "a very goodly day" the same segmentation as above could be applied and there would be three exact matches of a score 0.0 and one replacement match of "good" for "goodly" which by itself might be assigned a score of 0.5 and thus the total score for these sequences would be 0.5.

In the embodiment described above, matcher engine 216 includes a set of rules that are represented by a list. That list can be indexed by a pair of numbers. The index pair 1, 1 is a 1-to-1 replacement rule. The index 1,0 is a one-for-empty insertion (deletion rule). A 2,3 indexed rule compares two elements to three elements. As a result, embodiments of matcher engine 216 having an arbitrary set of such indexed rules allow for the matching of an n-element sequence to an m-element sequence, for arbitrary values of m can be implemented using myriad different segmentations into a set of local matches and scores. In an embodiment of matcher engine 216 described herein, matching the total score for the match is the closest, in this case lowest value match for all applied segmentations.

The rules indexed by these pairs (e.g. 1,0, 1,1, 2,3) refer to rules that are used to score local matches. In a simple example, this can be a fixed value such as 1.0 or 1.5. In embodiments, scores can result from further evaluation of the items being compared, such as assigning a local score of 1.0 to "good" and "bad" vs. a local score of 0.5 to "good" and "goodly". In embodiments, a rule for a local match can be position dependent. For example, an insertion error in the middle of the sequence can be scored higher or lower than the same or equivalent insertion at the end of a sequence. Thus the indexed rules both define how to score a local match and also define the possible ways to segment an n-element sequence match to an m-element sequence. Matcher engine 216 can comprise a dynamically-loaded set of rules that are appropriate for a particular context.

The following examples are provided by way of illustration and are in no way limiting on the scope of the invention.

An insertion rule (1,0) can be assigned a simple fixed value of 1.0.

An insertion rule (1,0) can be assigned a simple fixed value of 1.0 unless it is stand-alone punctuation, then 0.3 is assigned.

A replacement rule (1,1) is assigned a fixed value of 1.0 unless one word contains the other (cat, cats) then 0.2 or if the words are equivalent in the given context (e.g. 2, two and II) in which case a value of 0.0 is assigned.

A 3-2 replacement rule is assigned a fixed value of 3.5 unless the 3 to 2 replacement is of the form "A, B" replaces "B, A" has a value of 0.0. Note this takes common word order replacements such as "hypertension, essential" and "essential hypertension" into account.

In certain embodiments, a special insertion rule 1,0 only applies to the end of a match and only if the inserted word has the form "(nnnn)" where nnnn is a code such as a CPT code. This can be used to match a return from the EHR interface of "CT SCAN OF HEAD OR BRAIN WITH CONTRAST (70460)" to original text in the note of "CT SCAN OF HEAD WITH CONTRAST."

Correction engine 206 is configured to determine if and when a user should be advised of a possible ambiguity for a target phrase when there are multiple choices for items to be entered into the EHR corresponding to a single segment or overlapping segments of the encounter clinical document.

In an embodiment, the list presented to the user by correction engine 206 includes all matches coming back from EHR query engine 208 that match the object from the general medical query 220 with a score below a threshold number. In an embodiment, the threshold number can be a predefined value, can be associated with a particular EHR query engine 208, or it can be a user settable option such as in a preference list. The list presented to the user is sorted with lower (closer)) matches appearing first in order of decreasing closeness such that the option the user will actually want is closest to the top and thus easier to select by voice command (e.g. the user can say "choose 1") or by other user interface, such as by clicking.

Correction engine 206 can be configurable by an option setting to display more or less items based on a set of criterion so the user has control on incorrect entries compared to having to correct additional or fewer entries. As described herein, correction engine 206 utilizes the scores produced by the matcher engine 216. In other embodiments, correction engine 206 can further utilize the bias generated by learning engine 222, as will be described. In still other embodiments, correction engine 206 can utilize general medical query engine 220 data, and particularly, whether general medical query engine 220 was able to assign a standard code to a given clinical item with some level of confidence. If it is determined that the proper assignment of value to a clinical item is ambiguous based on its criterion, correction engine 206 can submit the possible choices of such values to presentation engine 210 for display and selection to the user.

Dictation management subsystem 200 further comprises presentation engine 210. In other embodiments, presentation engine 210 can be implemented in dictation user interface 102 as depicted in FIG. 1. Presentation engine 210 is configured to present the user with dictation management prompts according to parser engine 204, correction engine 206, and EHR query engine 208.

Presentation engine 210 comprises the display visible to the user, or the user interface of dictation management subsystem 200. Presentation engine 210 can present the user login forms, patient and appointment selection, as well as other EHR system-specific prompts. In embodiments, initiating an instance with this data can allow the user to easily begin entering data into the desired clinical document. Presentation engine 210 is further configured to display the text of the original encounter clinical document. Presentation engine 210 is further configured to display the current best guess for clinical items identified in the encounter note. As needed, presentation engine 210 is configured to display information submitted by correction engine 206 to make the process of resolving possible ambiguities efficient and effortless for the user. Color and other visual clues (e.g. font style) can be implemented by presentation engine 210 as feedback to make the user aware of the state and quality of information as the information is processed by the system. For example, green can be used to indicate a confident identification of a clinical item, whereas orange may visually cue an ambiguity.

In an embodiment, dictation management subsystem 200 further comprises learning engine 222. Learning engine 222 is configured to record results of the user interacting with the system or the interaction of the various sub-engines of dictation management subsystem 200. For example, when a user makes a selection among a list of possibly ambiguous identifications of a clinical item in the text of the encounter clinical document, learning engine 222 records the list and the selection. If the same sequence of text is encountered in a subsequent clinical document or even in the same clinical document, learning engine 222 can be used to inform or bias the scoring values assigned by the matcher engine 216 and/or effect the operation of the correction engine 206 so the user will be more likely to be able to accept the initially-selected choice or one of the first few choices for the subsequent ambiguity. In some embodiments, the user is not presented a list for the subsequent ambiguity at all.

In an embodiment, when a user selects from a multitude of choices for an ambiguous match, learning engine 222 can record that choice and store the pair, the original text that was matched, and the matching text that was chosen as a pair in a separate section of local database 218. Later, when processing the same text or text in some other encounter, if the previously-matched text is to be presented for selection of choices for a match, the previously-made user choice can be used to alter the score of the presented items (the second items in the pair). For example, depending on the biasing adjustment, the second items presented can change positions in the sorted list. Learning engine 222 biasing in this way can move an item higher, move an item to the top, or even cause the correction engine 206 to forego presenting that item for choice to the user at all based on, for example, the match score and its relation to the next best match.

Dictation management subsystem 200 further comprises cache engine 214. Cache engine 214 is configured to record recent results of queries to the general medical query engine 220 or EHR query engine 208. Cache engine 214 can store the results of such queries using some combination of recently used or frequently used queries and serves to make the most common queries faster. In an embodiment, cache engine 214 can be separate from learning engine 222, as depicted in FIG. 3. In other embodiments, cache engine 214 and learning engine 222 can be combined. This allows for increased user-response times.

Figure 4:
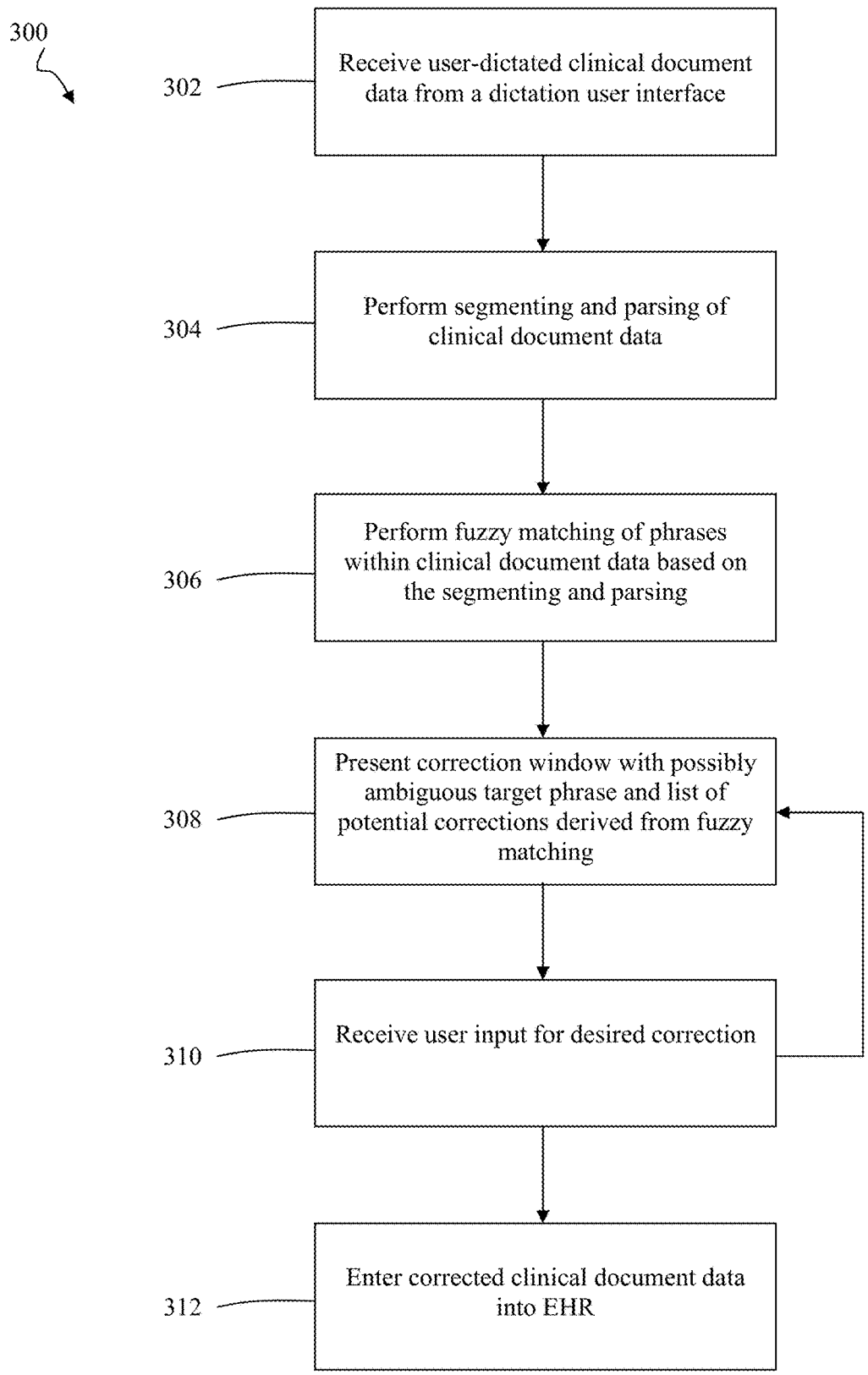
FIG. 4 is a flowchart of a method for managing dictation into an EHR with a dictation management subsystem, according to an embodiment.

Referring to FIG. 4, a flowchart of a method 300 for managing dictation into an EHR with a dictation management subsystem is depicted, according to an embodiment.

Additional reference to FIG. 1 is made for context of the hardware and software components implementing the method.

Method 300 generally comprises, at 302, receiving user-dictated clinical document data from a dictation user interface. For example, dictation user interface 102 can be utilized to receive dictated clinical document data.

At 304, segmentation and parsing of the clinical document data is performed. For example, the text can be parsed into individual words or phrases. In embodiment, section headers of the SOAP note for each word or phrase can be identified. Parsing can query local and remote databases for common language words and phrases, and common medical terminology. Such parsing and segmentation allows for continuous speech with only modestly constrained grammar. Further, neighborhood context is provided for the segmented and parsed phrases, which in turn drives queries more intelligently by using the characteristics of the section of the SOAP note that is being dictated.

At 306, fuzzy matching of phrases within the clinical document data is performed based on the segmenting and parsing of 304. In embodiments, matching can be conducted against online databases, such as local and publicly available general medical databases. In embodiments, matching can be conducted utilizing the particular EHR system for which the system implementing the method is interfacing. Such fuzzy matching at 306 generates a non-exact match that minimizes the amount of additional post-match user interaction and thus at least in part takes the place of natural language processing.

At 308, a correction window is presented to the user. The correction window can present a possibly ambiguous target phrase and a list of potential corrections derived from the fuzzy matching at 306.

At 310, user input for the desired correction to the possibly ambiguous target phrase is received. For example, the user can select the correction from a list of possible corrections. As shown in FIG. 4, method 300 processing can recursively return to 308 for additional possibly ambiguous target phrase presentation.

At 312, once all corrections have been made, the corrected clinical document data is entered into the EHR. For example, dictation management subsystem 104 can transmit or otherwise save the corrected clinical document data into EHR system 106a, or EHR database 108a.

Figure 5A:
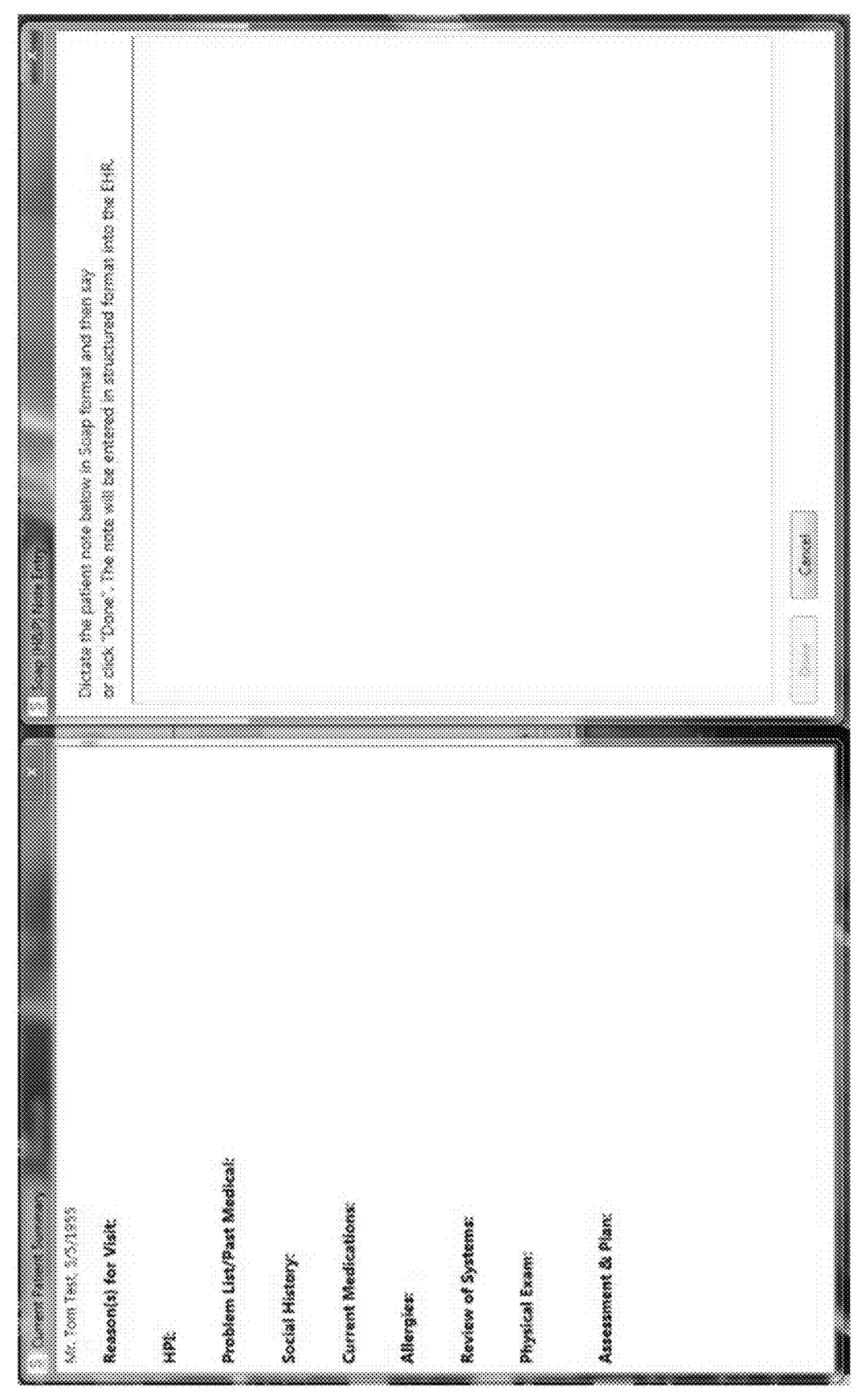

Referring to FIG. 5A, a screenshot of a patient summary window and a SOAP note dictation entry window is depicted, according to an embodiment. The patient summary window and SOAP note dictation entry window can be displayed to the user after the user has accessed the system, logged in, and selected an appointment (which can also select a patient, in embodiments).

Figure 5B:
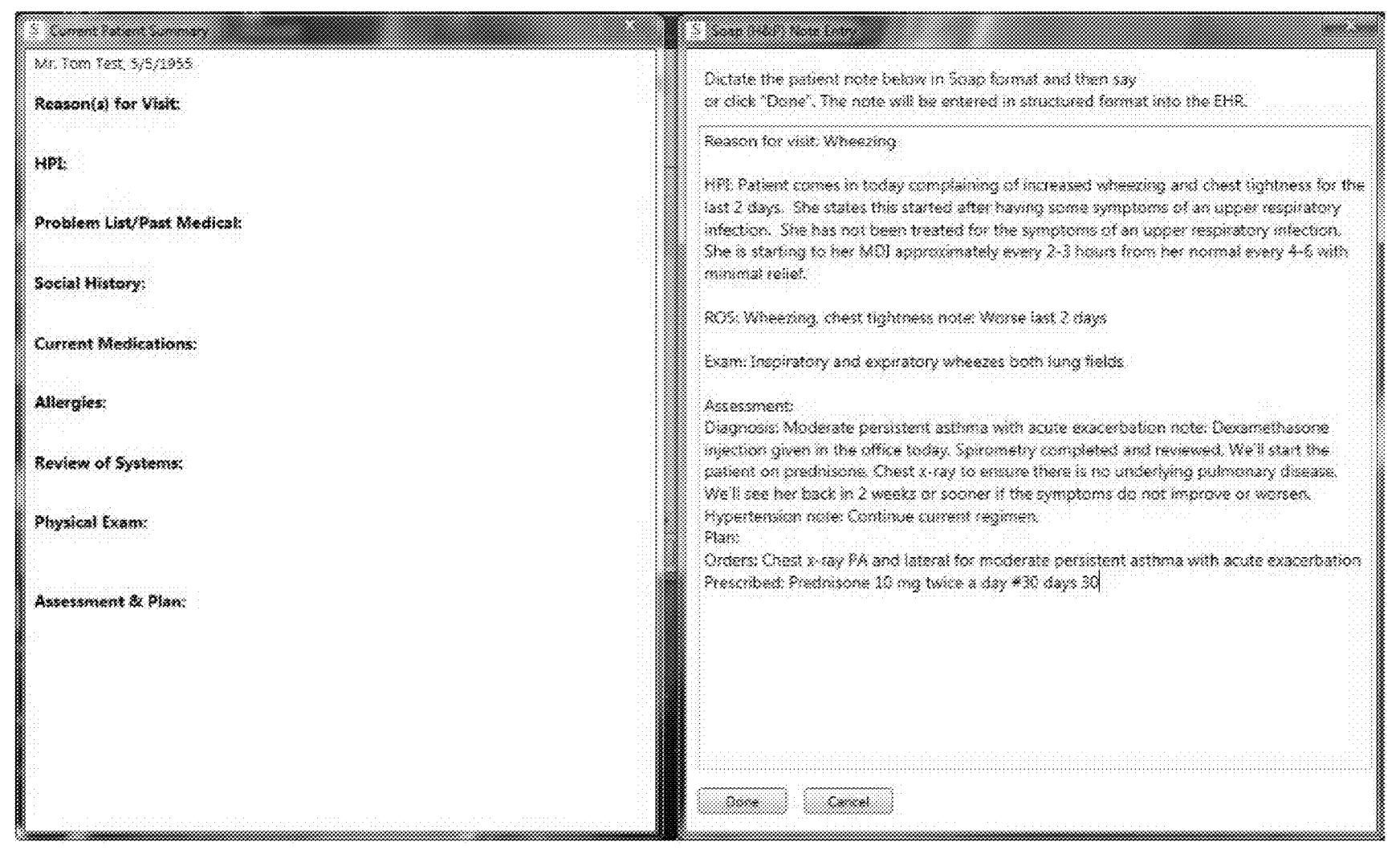

Referring to FIG. 5B, a screenshot of a patient summary window and a SOAP note dictation entry window with text entered using a dictation interface is depicted, according to an embodiment. The filled-in SOAP note dictation entry window is displayed after the user has dictated using continuous speech. In embodiments, the user can use dictation user interface 102 to describe his impressions of the encounter with the patient. Text representing the speech is correspondingly entered in the SOAP note entry window.

Figure 5C:
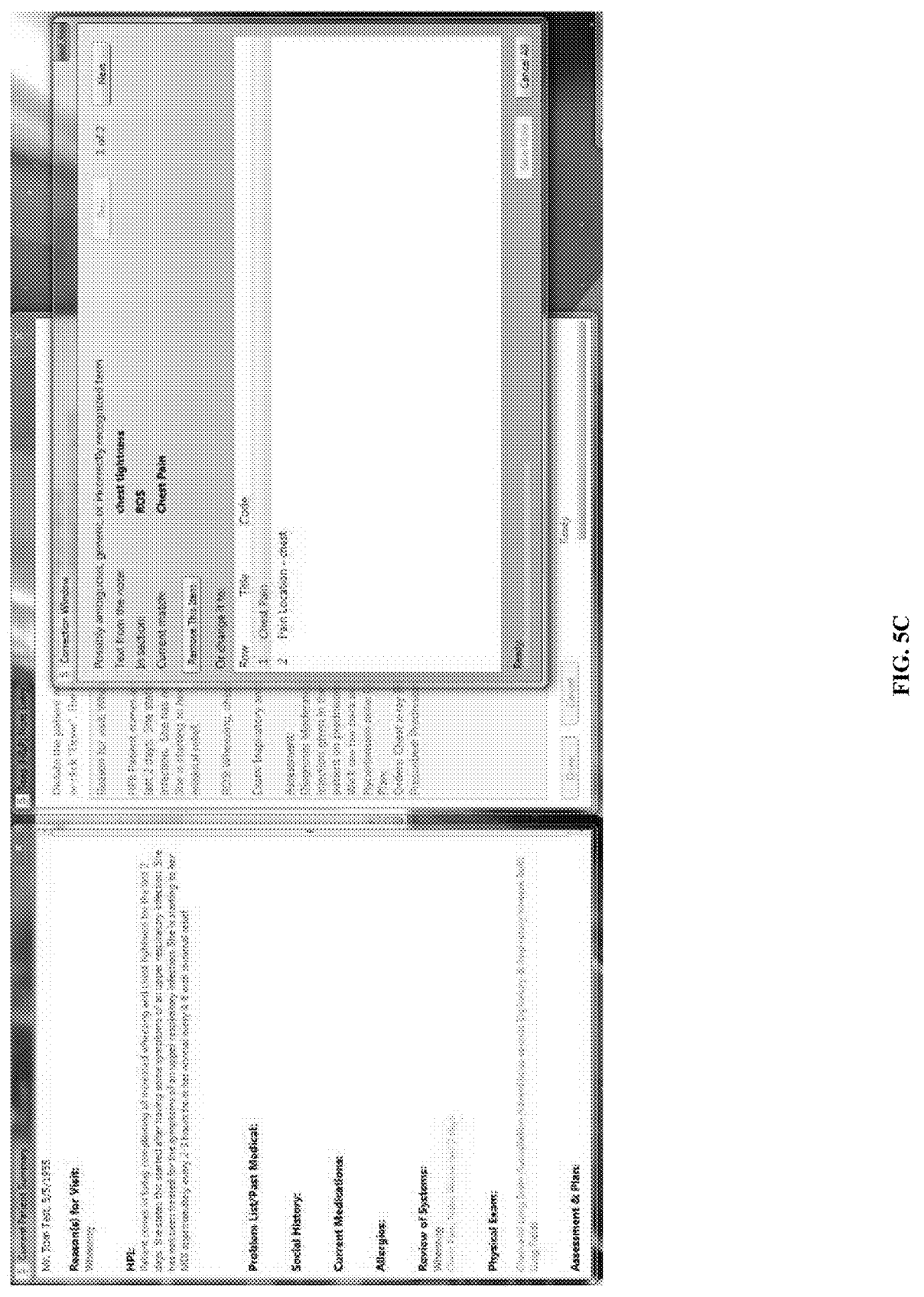

Referring to FIG. 5C, a screenshot of a patient summary window and a SOAP note dictation entry window in the background and a correction window for a first possibly ambiguous, generic, or incorrectly recognized term in the foreground is depicted, according to an embodiment. In embodiments, the correction window is presented after the user has spoken the command "Done" (or an equivalent) or clicked the "Done" (or equivalent) button to signal that the text should be processed. Accordingly, after processing, some items are parsed and matched from the note text and are ready to enter into the EHR with no correction. These can also be color-coded such as green for "Wheezing." In some cases, the text can have multiple interpretations that have equivalent (close) matching scores. These multiple interpretation terms can be presented to the user to correct or even remove. For example, the term "chest pain" is color-coded orange in the patient summary window (via the presentation engine) and is accordingly submitted to the presentation engine for correction by the user with the correction window.

Figure 5D:
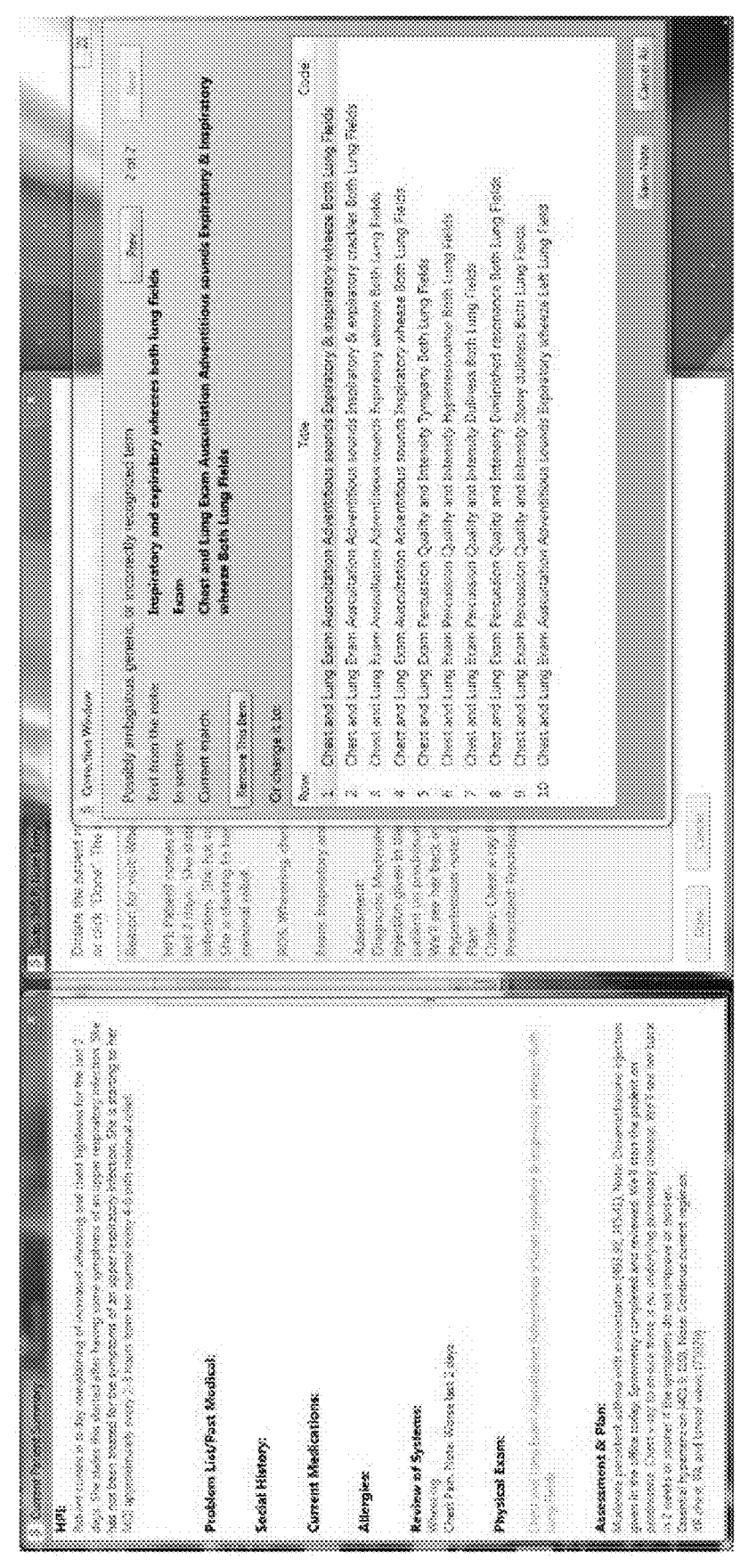

Referring to FIG. 5D, a screenshot of a patient summary window and a SOAP note dictation entry window in the background and a correction window for a second possibly ambiguous, generic, or incorrectly recognized term in the foreground is depicted, according to an embodiment. In FIG. 5D, the user has selected his choice for the term "chest pain." In embodiments, the term can accordingly be color-coded as changed in green on the patient summary window. The correction window can then display the next term that may need correction.

Figure 5E:
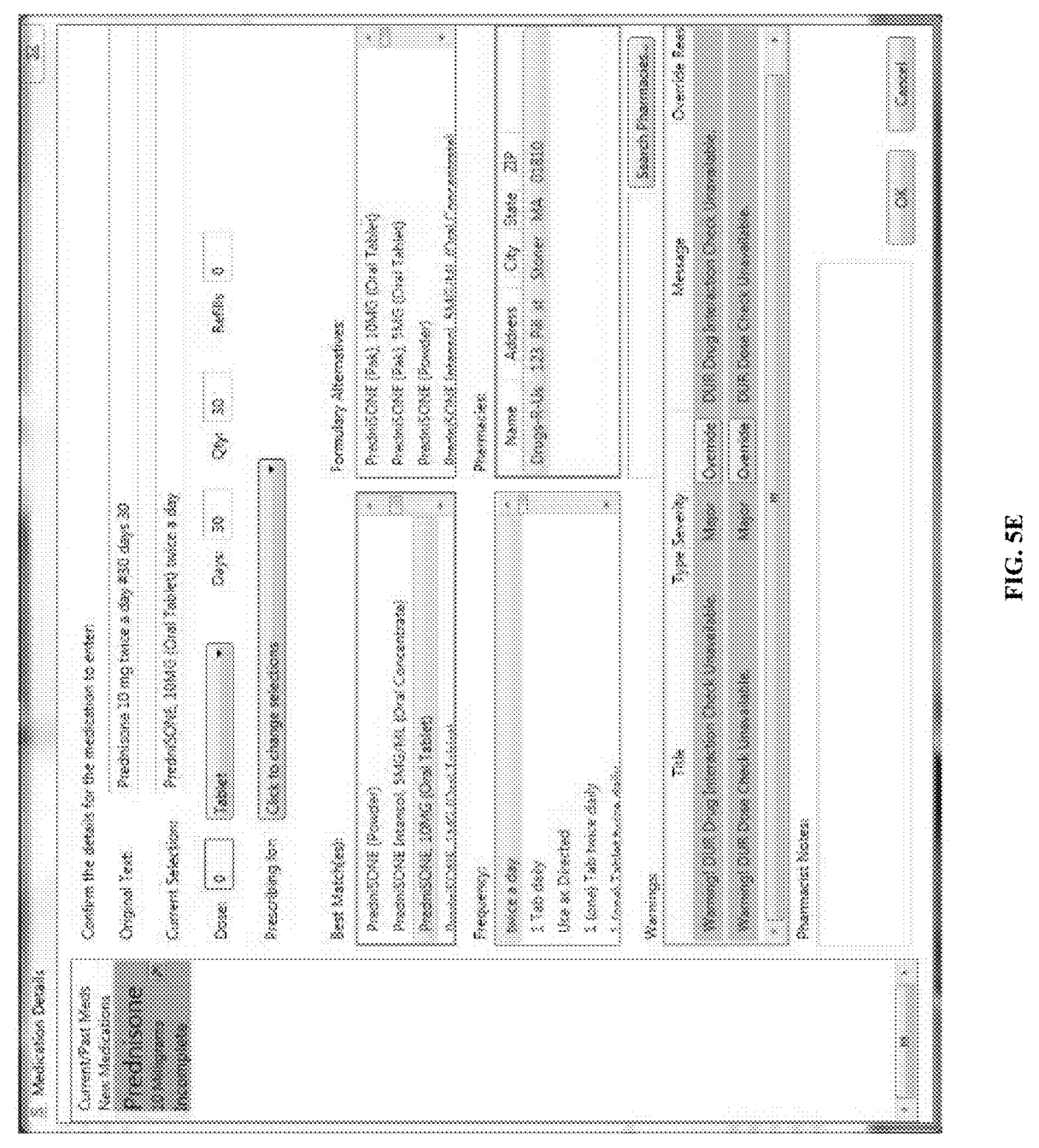

Referring to FIG. 5E, a screenshot of a medication details window is depicted, according to an embodiment. The medication details window is presented after the user has corrected all necessary ambiguous items with the exception of medications (historical and/or prescribed). The medications details window in FIG. 5E is then presented to correct medications dictated by the user. In embodiments, presentation engine is utilized to present this entry screen to the user.

Figure 5F:
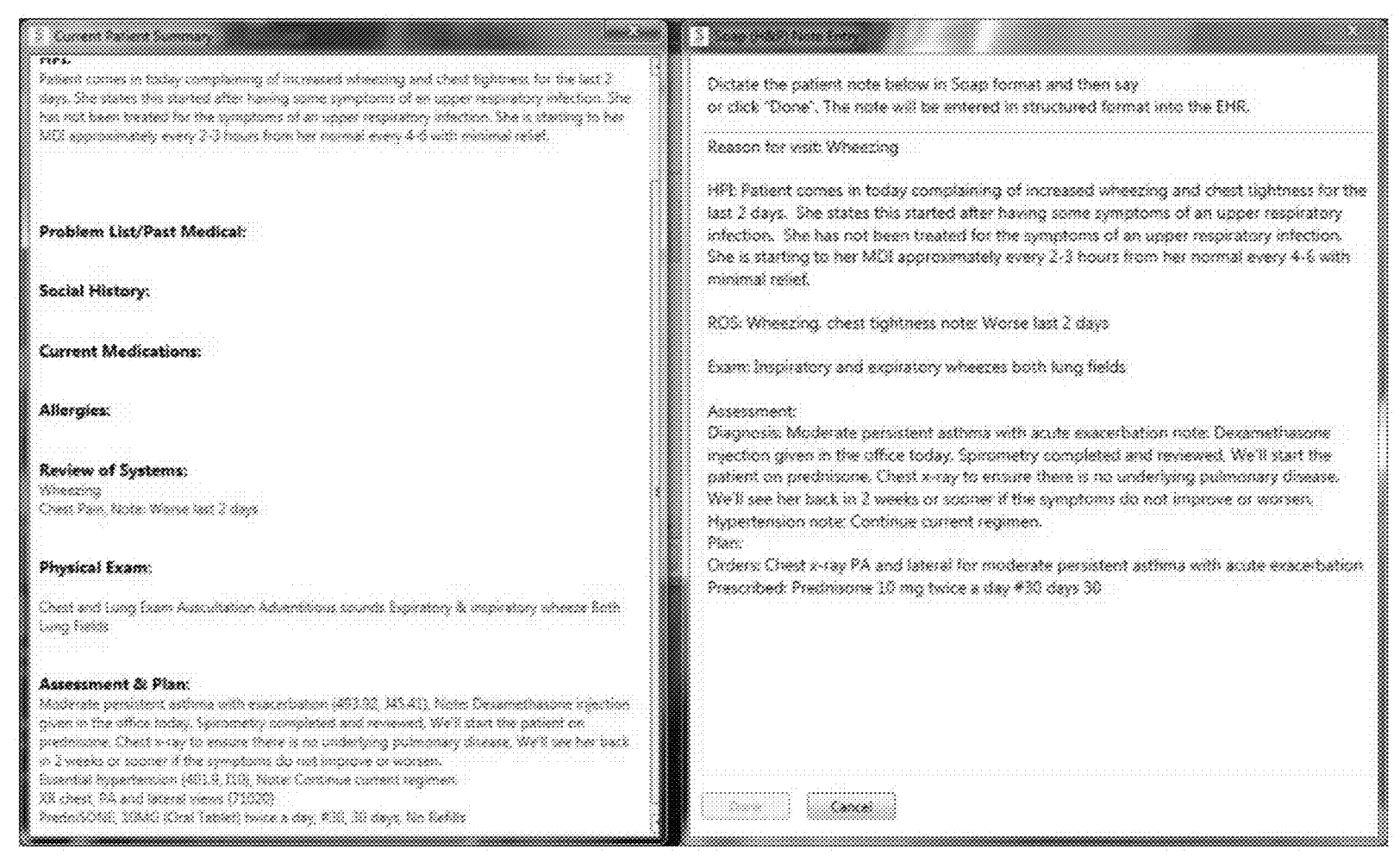

Referring to FIG. 5F, a screenshot of a corrected patient summary window and a SOAP note dictation entry window for entry into an EHR is depicted, according to an embodiment. The corrected patient summary is presented after the user has corrected all items. In embodiments, the information corresponding to the items in the corrected patient summary window are entered into the EHR.

Figure 6:
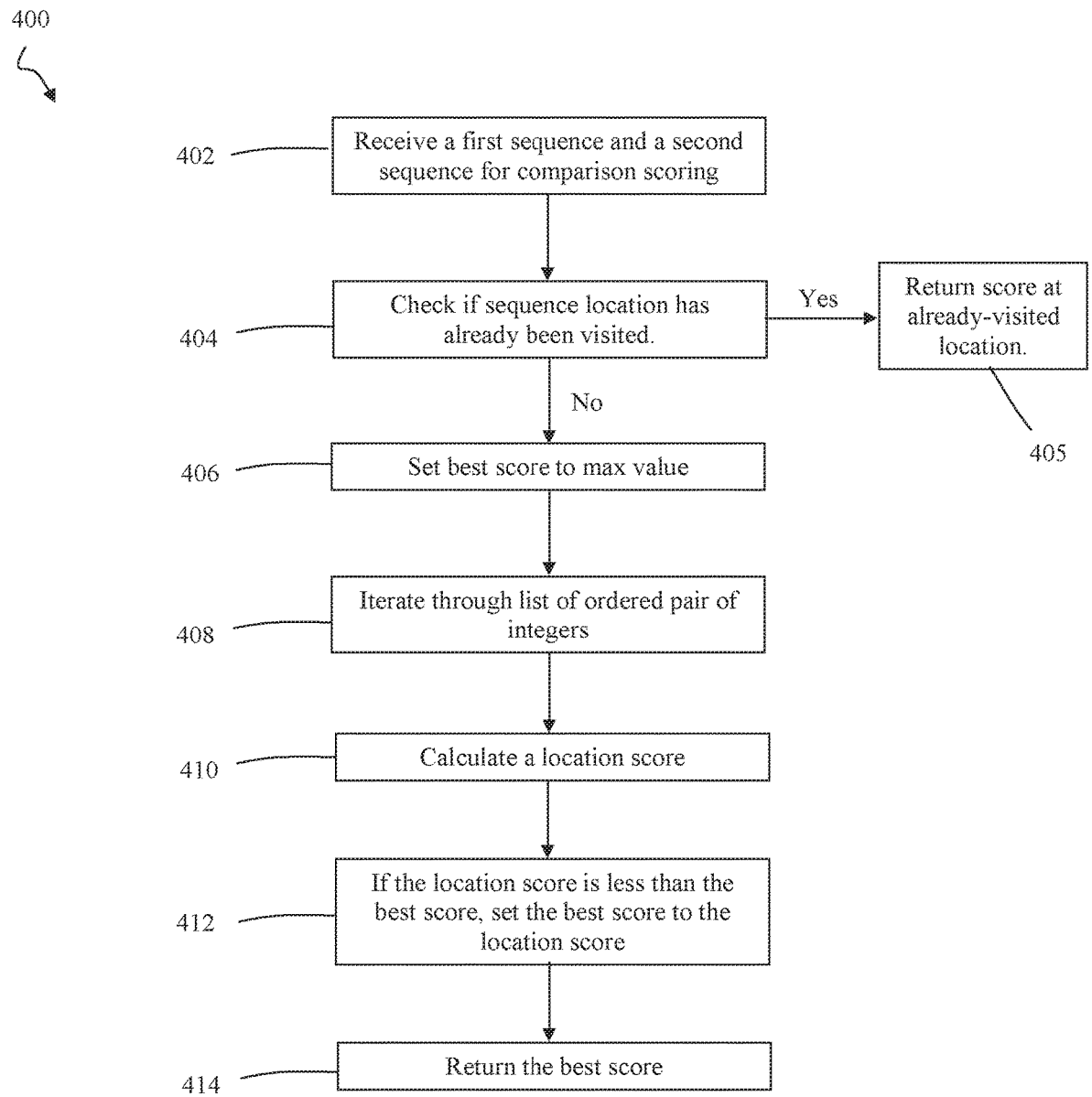
FIG. 6 is a flowchart of a matcher engine walking method, according to an embodiment.

Returning to matcher engine 216, a number of algorithms can be utilized in matcher scoring. Referring to FIG. 6, a flowchart of a matcher engine 216 walking method 400 is depicted, according to an embodiment. Walking method 400 can be utilized for traversing sequences to be scored.

Figure 7:
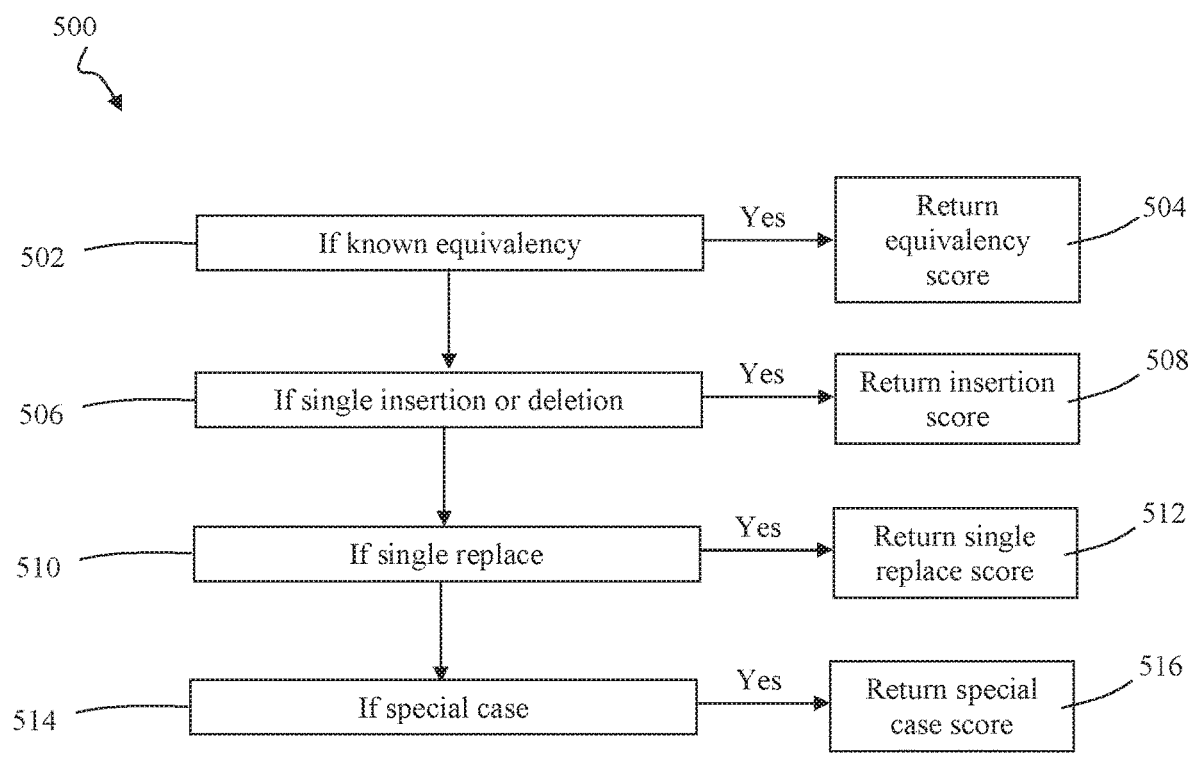
FIG. 7 is a flowchart of a matcher engine scoring method, according to an embodiment.

Method 400 operates by scoring two arrays of items (such as words), which can be varying lengths. In an embodiment, lower match scores are better such that 0 is a perfect match. For example, at 402, a first sequence and a second sequence (such as two arrays) are received. At 404, a check is conducted to determine if the sequence location has already been visited. If it has already been visited (and scored), there is no need to rescore, so the score at that matrix location is returned at 405. Otherwise, at 406, a best score variable is set to a max value. In an embodiment where lower matches are better, the max value can be 100. At 408, the sequences of ordered pairs of integers are iterated through. For example, the ordered pairs define a walking path that limits the squares that can be visited. In an embodiment, an offset into the arrays can be utilized. In other embodiments, the arrays are entered at [0, 0] without an offset. At 410, a location score is calculated. In embodiments, an ordered pairs list utilized for array walking as well as the scoring method described in FIG. 7 are set before matching. In embodiments, the ordered pairs list and scoring method can be context dependent. At 412, if the location score is less than the best score, the best score is set to the location score. At 414, the best score is returned for each location.

Figure 8A:
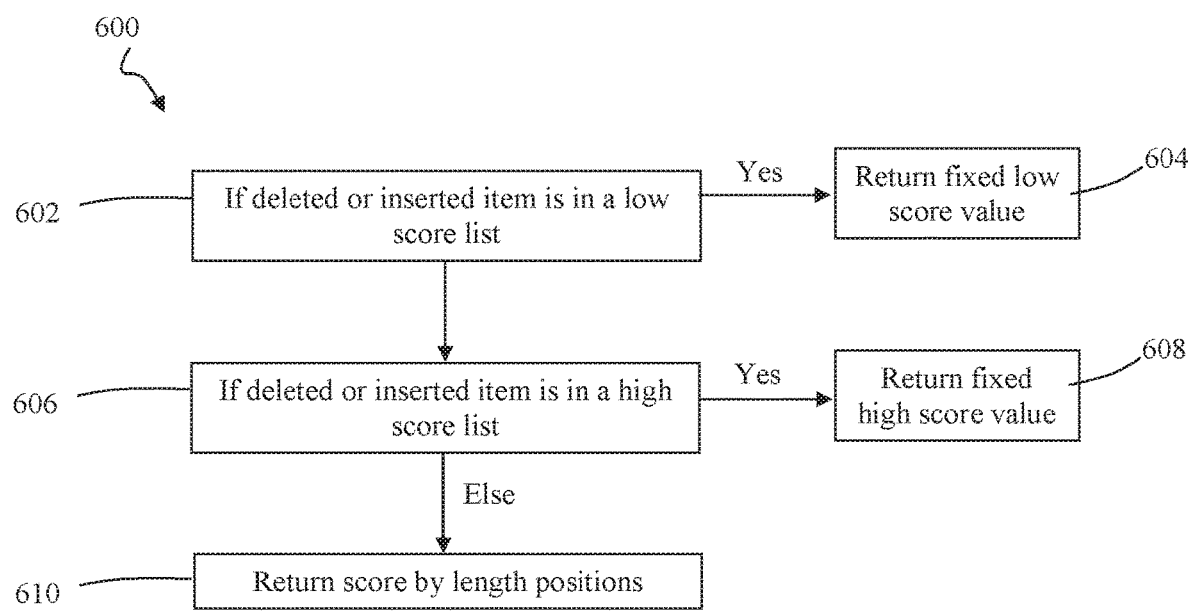
FIG. 8A is a flowchart of an insertion/deletion scoring sub-method, according to an embodiment.
Figure 8B:
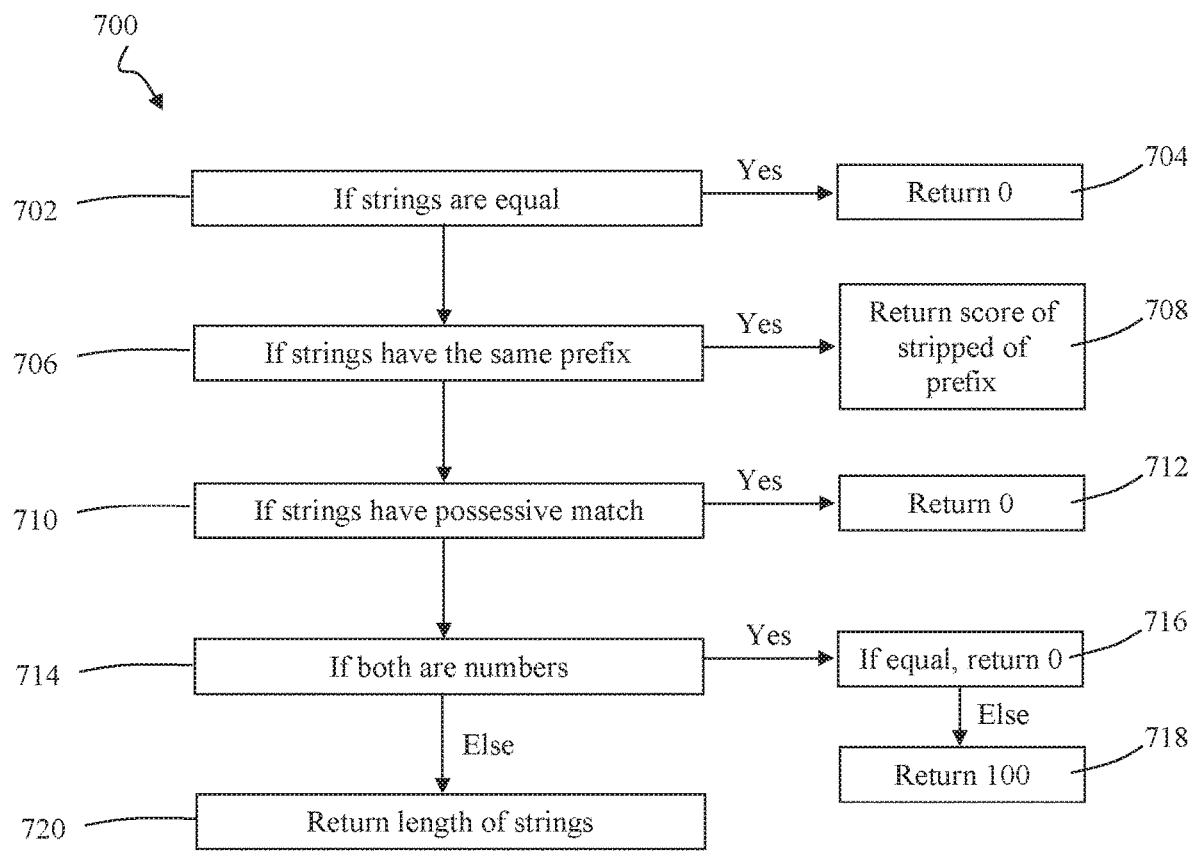
FIG. 8B is a flowchart of a single replace scoring sub-method, according to an embodiment.
Figure 8C:
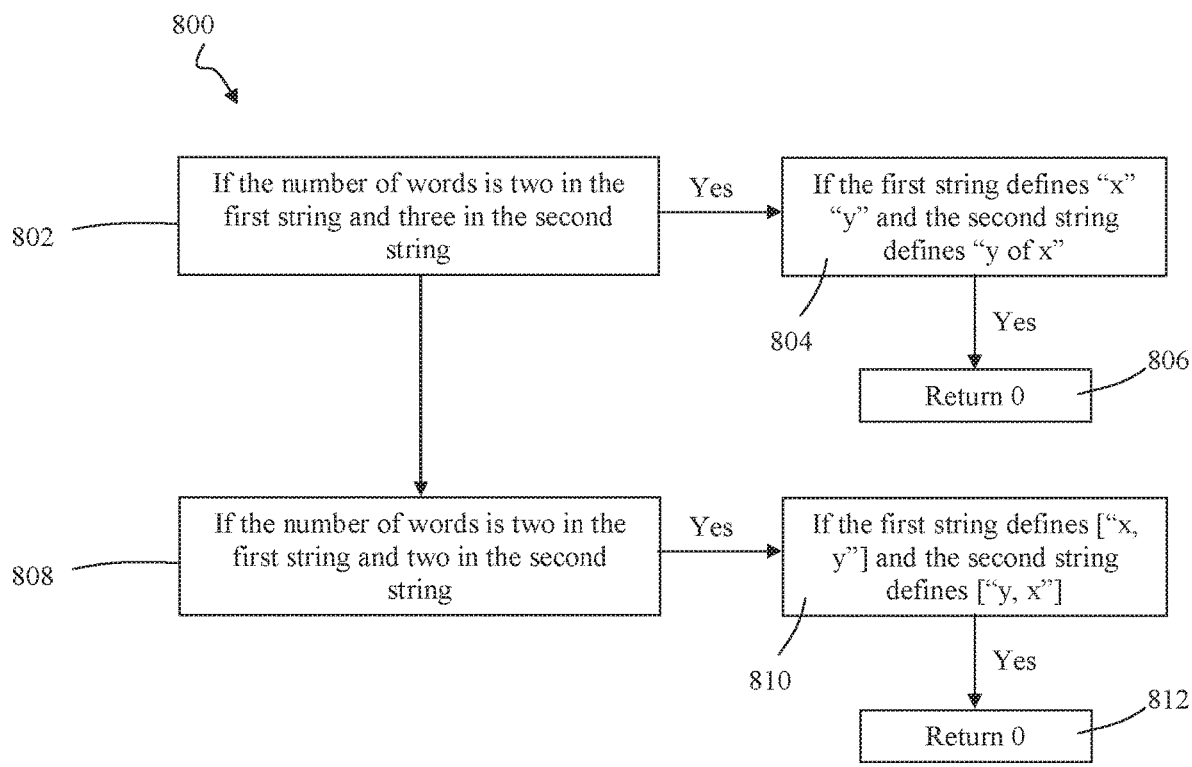
FIG. 8C is a flowchart of a special case scoring sub-method, according to an embodiment.

Referring to FIG. 7, a flowchart of a matcher engine scoring method 500 is depicted, according to an embodiment. As mentioned with respect to FIG. 6, scoring method 500 can be context dependent and carry its own rules. In an embodiment, method 500 compares a sequence of elements at position m to a second sequence of elements at position n using a variety of sub-methods, as will be described with respect to FIGS. 8A-8C.

At 502, if the two values reflect a known equivalency, an equivalency score is returned at 504. For example, the abbreviation "CBC" is a known equivalent to "complete blood count." In another example, synonyms such as "cancer" and "carcinoma" are known equivalencies. In such cases, 0 is returned, indicating a perfect match. In other embodiments, a non-zero number can be returned, depending on the relative equivalency.

Otherwise, at 506, if the two values reflect a single insertion or single deletion, an insertion score is returned at 508. For example, referring to FIG. 8A, a flowchart of an insertion/deletion scoring sub-method 600 is depicted, according to an embodiment. At 602, if the deleted or inserted item is contained within a low score list, a fixed low score value is returned at 604. At 606, if the deleted or inserted item is contained within a high score list, a fixed high score value is returned at 608. In embodiments, the low score list or high score list can contain the values to be returned. In embodiments, both fixed low score value and fixed high score values can be context related. Otherwise, at 610, a scoring based on the length of the analyzed values is returned. In an embodiment, length can comprise the length of an expanded abbreviation, where appropriate.

Returning again to FIG. 7, at 510, if the two values reflect a single replacement, a single replacement score is returned at 512. For example, referring FIG. 8B, a flowchart of a single replace scoring sub-method 700 is depicted, according to an embodiment. At 702, if the strings being checked for a single replacement are equal, 0 is returned at 704. At 706, if the strings have the same prefix, the prefixes are stripped at 708 and the score of the remaining strings is calculated at 708. At 710, if the strings have a possessive match, such as "Hashimotos" and "Hashimoto's," 0 is returned at 712. At 714, if both strings reflect numbers, an evaluation at 716 is conducted. If they are both equal, 0 is returned. Otherwise, 100 is returned at 718. At 720, and similar to the default insertion score, only the length of the strings is charged as the score.

Returning again to FIG. 7, at 514, if the two values reflect a special case, a special case score is returned at 516. For example, referring to FIG. 8C, a flowchart of a special case scoring sub-method 800 is depicted, according to an embodiment. Sub-method 800 can handle special aspects of language. In embodiments, a comparison of "colon cancer" and "cancer of the colon" should be an exact match. At 802, if the number of words in the first string is two and the number of words in the second string is three, a check at 804 is conducted. If the first string defines "x" "y" and the second string defines "y of x", 0 is returned at 806. At 808, if the number of words is two in the first string and two in the second string, a check at 810 is conducted. If the first string defines "x, y" and the second string defines "y, x", return 0.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A system for dynamically-configurable SOAP (subjective, objective, assessment, and plan) note dictation, the system comprising:
  a computing platform including computing hardware of at least one processor, a memory operably coupled to the at least one processor, and configured to store instructions invoked by the at least one processor;
  instructions that, when executed on the computing platform, cause the computing platform to implement:
    a dictation user interface including an abstraction layer for programmatic access to a speech-to-text recognition component and configured to receive user-dictated clinical document data as a SOAP note; and
    a dictation management subsystem including:
      a segmenter engine configured to receive as input the user-dictated clinical document data and segment the clinical document data into a plurality of lines and tokens and identify a plurality of section headers for the SOAP note;
      a parser engine configured to receive the plurality of lines and tokens from the segmenter engine and access one or more databases limited by at least one characteristic of a particular section header for the SOAP note, the particular section header corresponding to a particular plurality of lines and tokens to match the plurality of lines and tokens to a plurality of meaningful medical phrases using fuzzy matching to create a plurality of exact match entries and at least one non-exact match entry, the fuzzy matching including at least one rule corresponding to the particular section header for the SOAP note;

a correction engine configured to determine possible ambiguities for the at least one non-exact match entry based on the fuzzy matching, and a presentation engine configured to present a correction window on a graphical user interface, the correction window including the at least one non-exact match entry and a list of potential corrections derived from the fuzzy matching, and receive a user-selection of one of the list of potential corrections for the at least one non-exact match entry that is used to generate corrected clinical document data for the SOAP note;

an electronic health record (EHR) query engine configured to enter the SOAP note including the corrected clinical document data and the plurality of exact match entries into an electronic health record.

2. The system of claim 1, wherein the dictation management subsystem further comprises a matcher engine configured to conduct fuzzy matching by scoring the plurality of lines and tokens against the plurality of meaningful medical phrases from the one or more databases.

3. The system of claim 2, wherein the matcher engine is further configured to conduct ranking a particular set of lines and tokens against the meaningful medical phrases to indicate a closeness of the particular set of lines and tokens to the plurality of meaningful medical phrases.

4. The system of claim 3, wherein the matcher engine is further configured to add at least one line or token to the particular set of lines and tokens and re-score the particular set of lines and tokens against the plurality of meaningful medical phrases.

5. The system of claim 3, wherein the matcher engine is further configured to remove at least one line or token from the particular set of lines and tokens and re-score the particular set of lines and tokens against the plurality of meaningful medical phrases.

6. The system of claim 2, wherein the matcher engine is further configured to compare the plurality of lines and tokens having an m-element sequence of items to one of the plurality of meaningful medical phrases having an n-element sequence of items, and wherein the scoring includes a measure of how the elements in the m-element sequence of items match the n-element sequence of items, and a measure of the how the ordering of the m-element sequence of items match the n-element sequence of items.

7. The system of claim 2, wherein the matcher engine is further configured with a set of rules, the set of rules used in scoring the plurality of lines and tokens against the plurality of meaningful medical phrases including at least one of:

a one-to-one replacement rule, a one-for-empty deletion rule, and a replacement rule.

8. The system of claim 1, wherein the correction engine determines the at least one non-exact match entries below a threshold value based on the fuzzy matching.

9. The system of claim 1, wherein the list of potential corrections derived from the fuzzy matching is sorted in order of decreasing closeness.

10. A machine-implemented method for dynamically-configurable SOAP (subjective, objective, assessment, and plan) note dictation for a computing system, the computing system including computing hardware of at least one processor and a memory operably coupled to the at least one processor, the method comprising:

presenting a dictation user interface with the computing hardware, the dictation user interface including an abstraction layer for programmatic access to a speech-to-text recognition component;

receiving user-dictated clinical document data as a SOAP note from the dictation user interface;

performing segmenting and parsing of the clinical document data with the computing hardware to generate a segmented and parsed clinical document dataset and identify a plurality of section headers for the SOAP note, the segmented and parsed clinical document dataset including a plurality of lines and tokens;

performing fuzzy matching on the plurality of lines and tokens with the computing hardware including implementing at least one rule corresponding to the particular section header for the SOAP note, the particular section header corresponding to a particular plurality of lines and tokens to determine known clinical entries and a set of non-exact match entries by comparison to a plurality of meaningful medical phrases limited by at least one characteristic of a particular section header for the SOAP note;

presenting a correction window on a graphical user interface with the computing hardware, the correction window including at least one non-exact match entry in the segmented and parsed clinical document dataset and a list of potential corrections derived from the fuzzy matching;

receiving a user-selection of one of the potential corrections for the at least one non-exact match entry that is used to generate corrected clinical document data; and entering, with the computing hardware, the known clinical entries and the corrected clinical document data as the SOAP note into an electronic health record (EHR).

11. The machine-implemented method of claim 10, wherein performing fuzzy matching further comprises scoring the plurality of lines and tokens against the plurality of meaningful medical phrases from the one or more databases.

12. The machine-implemented method of claim 11, wherein the scoring further comprises ranking a particular set of lines and tokens against the meaningful medical phrases to indicate the closeness of the particular set of lines and tokens to the plurality of meaningful medical phrases.

13. The machine-implemented method of claim 12, further comprising adding at least one line or token to the particular set of lines and tokens and re-scoring the particular set of lines and tokens against the plurality of meaningful medical phrases.

14. The machine-implemented method of claim 12, further comprising removing at least one line or token from the particular set of lines and tokens and re-scoring the particular set of lines and tokens against the plurality of meaningful medical phrases.

15. The machine-implemented method of claim 11, wherein the scoring further comprises comparing the plurality of lines and tokens having an m-element sequence of items to one of the plurality of meaningful medical phrases having an n-element sequence of items, wherein the scoring includes
- a measure of how the elements in the m-element sequence of items match the n-element sequence of items, and
- a measure of the how the ordering of the m-element sequence of items match the n-element sequence of items.

16. The machine-implemented method of claim 11, further comprising utilizing a set of rules for scoring the plurality of lines and tokens against the plurality of meaningful medical phrases including at least one of:
- a one-to-one replacement rule,
- a one-for-empty deletion rule, and
- a replacement rule.

17. The machine-implemented method of claim 10, wherein the at least one non-exact match entry is determined to be below a threshold value based on the fuzzy matching.

18. The machine-implemented method of claim 10, wherein the list of potential corrections derived from the fuzzy matching is sorted in order of decreasing closeness.

19. A system for dynamically-configurable note dictation, the system comprising:
- means for presenting a computing system, the computing system including computing hardware of at least one processor and a memory operably coupled to the at least one processor;
- means for presenting a dictation user interface, the dictation user interface including an abstraction layer for programmatic access to a speech-to-text recognition component;
- means for receiving user-dictated clinical document data from the dictation user interface;
- means for performing segmenting and parsing of the clinical document data with the computing hardware to generate a segmented and parsed clinical document dataset and identify a plurality of section headers for the SOAP note, the segmented and parsed clinical document dataset including a plurality of lines and tokens;
- means for performing fuzzy matching on the plurality of lines and tokens with the computing hardware including implementing at least one rule corresponding to the particular section header for the SOAP note, the particular section header corresponding to a particular plurality of lines and tokens to determine known clinical entries and a set of non-exact match entries based on at least one database query limited by at least one characteristic of a particular section header for the SOAP note;
- means for presenting a correction window on a graphical user interface with the computing hardware, the correction window including at least one non-exact match entry in the segmented and parsed clinical document dataset and a list of potential corrections derived from the fuzzy matching;
- means for receiving a user-selection of one of the potential corrections for the at least one non-exact match entry as corrected clinical document data; and
- means for entering, with the computing hardware, the known clinical entries and the corrected clinical document data into an electronic health record (EHR).

20. The system of claim 19, wherein the dictation management subsystem further comprises a means for conducting fuzzy matching by scoring the plurality of lines and tokens against the plurality of meaningful medical phrases from the one or more databases, wherein the scoring further comprises a means for ranking a particular set of lines and tokens against the meaningful medical phrases to indicate the closeness of the particular set of lines and tokens to the plurality of meaningful medical phrases.

* * * * *